US012708313B2

(12) # United States Patent
Xu et al.

(10) Patent No.: US 12,708,313 B2
(45) Date of Patent: Aug. 18, 2026

(54) DEEP-LEARNING BASED PEAK DETECTION IN BIOLOGICAL SIGNAL

(71) Applicants: SONY GROUP CORPORATION, Tokyo (JP); SONY CORPORATION OF AMERICA, New York, NY (US)

(72) Inventors: Wanxin Xu, San Jose, CA (US); Ko-Kai Albert Huang, San Jose, CA (US)

(73) Assignees: SONY GROUP CORPORATION, Tokyo (JP); SONY CORPORATION OF AMERICA, New York, NY (US)

( * ) Notice: Subject to any disclaimer, the term of this patent is extended or adjusted under 35 U.S.C. 154(b) by 505 days.

(21) Appl. No.: 18/315,209

(22) Filed: May 10, 2023

(65) Prior Publication Data

US 2024/0188875 A1 Jun. 13, 2024

Related U.S. Application Data

(60) Provisional application No. 63/387,202, filed on Dec. 13, 2022.

(51) Int. Cl.
*A61B 5/352* (2021.01)
*A61B 5/00* (2006.01)
(Continued)

(52) U.S. Cl.
CPC .............. *A61B 5/352* (2021.01); *A61B 5/353* (2021.01); *A61B 5/355* (2021.01); *A61B 5/374* (2021.01); *A61B 5/7267* (2013.01)

(58) Field of Classification Search
CPC ......... A61B 5/352; A61B 5/353; A61B 5/355; A61B 5/374; A61B 5/7267; A61B 5/7203
See application file for complete search history.

(56) References Cited

U.S. PATENT DOCUMENTS

2017/0340228 A1* 11/2017 Dirkes ................. A61B 5/0245
2020/0105398 A1* 4/2020 Chen ....................... G06F 3/015
(Continued)

FOREIGN PATENT DOCUMENTS

CN 114010204 A 2/2022
EP 1886625 A1 * 2/2008 ............. A61B 5/352

OTHER PUBLICATIONS

Mjayarangan, et al., "RPnet: A Deep Learning approach for robust R Peak detection in noisy ECG", Indian Institute of Technology, Madras (IITM), India, Apr. 17, 2020, 4 pages.
(Continued)

*Primary Examiner* — Brian T Gedeon
(74) *Attorney, Agent, or Firm* — CHIP LAW GROUP

(57) ABSTRACT

An electronic device and a method for implementation for deep-learning based peak detection in biological signal. The electronic device receives a biological signal associated with a user. The electronic device detects a first peak and a first trough associated with the first peak, from the received biological signal. The electronic device applies a local search algorithm on the received biological signal. The electronic device refines the detected first peak and the first trough based on the application of the local search algorithm on the received biological signal. The electronic device determines a health condition associated with the user based on the refined first peak and the first trough.

18 Claims, 10 Drawing Sheets

(51) Int. Cl.

| | |
|---|---|
| ***A61B 5/353*** | (2021.01) |
| ***A61B 5/355*** | (2021.01) |
| ***A61B 5/374*** | (2021.01) |
| ***G06N 3/0455*** | (2023.01) |
| ***G16H 40/63*** | (2018.01) |
| ***G16H 50/20*** | (2018.01) |

(56) References Cited

U.S. PATENT DOCUMENTS

| | | | |
|---|---|---|---|
| 2021/0259560 | A1 | 8/2021 | Venkatraman |
| 2021/0378597 | A1 | 12/2021 | Amos |
| 2022/0015711 | A1 | 1/2022 | Kalidas |

OTHER PUBLICATIONS

Xu, et al., "A Scalable Deep-learning based Approach for R peak Detection in ECG Signal", Sony Corporation of America, San Jose, CA, USA, 2023, 1 page.

Application No. IN202231071330, "A Mobile Based Cardiac Health Monitoring System Using Deep Residual Network" National Institute of Technology, Rourkela, Dec. 10, 2022, 27 pages.

* cited by examiner

502A

Amplitue(mV)

4 2 0 -2 -4 -6

0 1000 2000 3000 4000

Time (Seconds)

502B

Amplitue(mV)

2 0 -2 -4 -6

0 1000 2000 3000 4000

Time (Seconds)

DEEP-LEARNING BASED PEAK DETECTION IN BIOLOGICAL SIGNAL

CROSS-REFERENCE TO RELATED APPLICATIONS/INCORPORATION BY REFERENCE

This application also makes reference to U.S. Provisional Application Ser. No. 63/387,202, which was filed on Dec. 13, 2022. The above stated patent applications are hereby incorporated herein by reference in their entirety

FIELD

Various embodiments of the disclosure relate to biological signals. More specifically, various embodiments of the disclosure relate to an electronic device and a method for deep-learning based peak detection in biological signal.

BACKGROUND

Advancements in sensors have led to development of biomedical devices to detect biological signals such as, electroencephalogram (EEG), electrocardiogram (ECG), electromyogram (EMG), electrooculogram (EOG), and the like. The detected biological signal may be then analyzed to determine a condition of an organ of a patient associated with the biological signal. For example, the EEG may be used to determine a condition of a brain of the patient, the ECG may be used to determine a condition of a heart of the patient, and the EMG may be used to determine a condition of muscles of the patient. Typically, the biological signals may be manually analyzed, which may be a time consuming and labor-intensive task. Furthermore, often specific peaks of the biological signal may need to be identified to determine the condition of the organ. Failure to detect the specific peak or inaccurate detection of the specific peak may often result in erroneous prediction of a health condition of the patient.

Limitations and disadvantages of conventional and traditional approaches will become apparent to one of skill in the art, through comparison of described systems with some aspects of the present disclosure, as set forth in the remainder of the present application and with reference to the drawings.

SUMMARY

An electronic device and method for deep-learning based peak detection in biological signal is provided substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
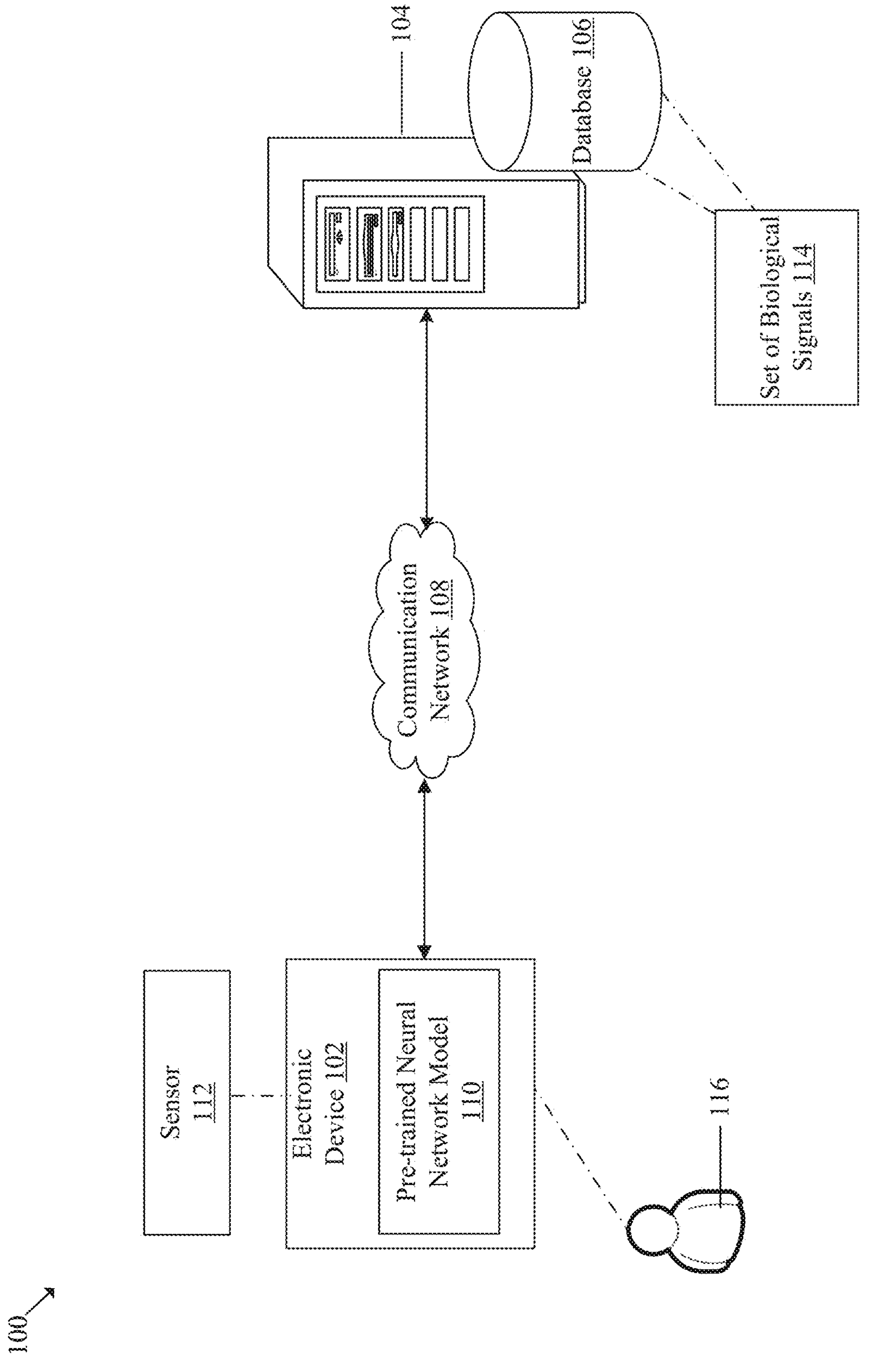
FIG. 1 is a block diagram that illustrates an exemplary network environment for deep-learning based peak detection in biological signal, in accordance with an embodiment of the disclosure.

The following described implementation may be found in an electronic device and method for deep-learning based peak detection in biological signal. Exemplary aspects of the disclosure may provide an electronic device that may receive a biological signal associated with a user. Next, the electronic device may detect a first peak and a first trough associated with the first peak, from the received biological signal. Thereafter, the electronic device may apply a local search algorithm on the received biological signal. Based on the application of the local search algorithm on the received biological signal, the electronic device may refine the detected first peak and the first trough. Based on the refined first peak and the first trough, the electronic device may determine a health condition associated with the user.

Typically, variety of sensors may be used to measure biological signals such as, electroencephalogram (EEG), electrocardiogram (ECG), electromyogram (EMG), electrooculogram (EOG), and the like, associated with a patient. The measured biological signal may be then analyzed to determine a condition of an organ of the patient. For example, the EEG may be used to determine a condition of a brain of the patient, the ECG may be used to determine a condition of a heart of the patient, and the EMG may be used to determine a condition of muscles of the patient. The analysis of the biological signal manually may be time consuming and labor-intensive task. Furthermore, often, specific peaks of the biological signal may need to be identified to determine the condition of the organ. For example, R-peak detection in the ECG may be crucial and may be a fundamental step for heart rate variability analysis (HRV), early diagnosis of certain heart diseases, and additional ECG-based analysis. However, existing R-peak detectors may suffer from noise and irregularities in ECGs. Thus, the existing R-peak detectors may detect false R-peaks. Failure to detect an accurate R-peak may often result in erroneous prediction of a health condition.

The electronic device of the present disclosure may provide an automatic and robust peak detection framework for a noisy and irregular biological signal. In order to do so, the electronic device may receive the biological signal associated with the user. Thereafter, in some embodiments, the electronic device may apply a low-pass filter on the received biological signal to remove a noise component from the received biological signal. Based on the removal of the noise component from the received biological signal, the electronic device may determine a denoised signal. Upon determination of the denoised signal, the electronic device may detect the first peak and the first trough. Thus, the detected first peak and the detected first trough may be immune to noise component prevalent in the received biological signal. Further, the electronic device may refine the detected first peak and the first trough based on the application of the local search algorithm on the received biological signal. The refined first peak and the first trough may be thus optimal. Based on the refined first peak and the first trough, the electronic device may determine the health condition associated with the user. Since the refined first peak and the first trough may be optimal, the determined health condition may be accurate. The disclosed electronic device may thereby enable a robust and efficient determination of the health condition of the user. Therefore, the disclosed electronic device may be incorporated in applications such as, intelligent medical and wearable devices, to monitor health of patients and provide an early diagnosis of diseases, such as, cardiovascular diseases (CVDs).

FIG. 1 is a block diagram that illustrates an exemplary network environment for deep-learning based peak detection in biological signal, in accordance with an embodiment of the disclosure. With reference to FIG. 1, there is shown a network environment 100. The network environment 100 may include an electronic device 102, a server 104, a database 106, and a communication network 108. The electronic device 102 may include a pre-trained neural network model 110. A sensor 112 may be associated with the electronic device 102. In FIG. 1, there is further shown a set of biological signals 114 that may be stored in the database 106. There is further shown a user 116, who may be associated with and/or operate the electronic device 102.

The electronic device 102 may include suitable logic, circuitry, interfaces, and/or code that may be configured to receive a biological signal associated with the user 116. The electronic device 102 may detect a first peak and a first trough associated with the first peak, from the received biological signal. The electronic device 102 may apply a local search algorithm on the received biological signal. The electronic device 102 may refine the detected first peak and the first trough, based on the application of the local search algorithm on the received biological signal. The electronic device 102 may determine a health condition associated with the user 116 based on the refined first peak and the first trough. Examples of the electronic device 102 may include, but are not limited to, a computing device, a smartphone, a cellular phone, a mobile phone, a gaming device, a mainframe machine, a server, a computer workstation, a machine learning device (enabled with or hosting, for example, a computing resource, a memory resource, and a networking resource), a wearable device with an inbuilt bio-medical sensor, a bio-medical device, and/or a consumer electronic (CE) device.

The server 104 may include suitable logic, circuitry, and interfaces, and/or code that may be configured to receive the biological signal associated with the user 116. The server 104 may detect the first peak and the first trough associated with the first peak, from the received biological signal. The server 104 may apply the local search algorithm on the received biological signal. The server 104 may refine the detected first peak and the first trough based on the application of the local search algorithm on the received biological signal. The server 104 may determine the health condition associated with the user 116 based on the refined first peak and the first trough.

The server 104 may be implemented as a cloud server and may execute operations through web applications, cloud applications, HTTP requests, repository operations, file transfer, and the like. Other example implementations of the server 104 may include, but are not limited to, a database server, a file server, a web server, a media server, an application server, a mainframe server, a machine learning server (enabled with or hosting, for example, a computing resource, a memory resource, and a networking resource), or a cloud computing server.

In at least one embodiment, the server 104 may be implemented as a plurality of distributed cloud-based resources by use of several technologies that are well known to those ordinarily skilled in the art. A person with ordinary skill in the art will understand that the scope of the disclosure may not be limited to the implementation of the server 104 and the electronic device 102, as two separate entities. In certain embodiments, the functionalities of the server 104 can be incorporated in its entirety or at least partially in the electronic device 102 without a departure from the scope of the disclosure. In certain embodiments, the server 104 may host the database 106. Alternatively, the server 104 may be separate from the database 106 and may be communicatively coupled to the database 106.

The database 106 may include suitable logic, interfaces, and/or code that may be configured to store the set of biological signals 114. The database 106 may be derived from data off a relational or non-relational database, or a set of comma-separated values (csv) files in conventional or big-data storage. The database 106 may be stored or cached on a device, such as a server (e.g., the server 104) or the electronic device 102. The device storing the database 106 may be configured to receive a query for the biological signal from the electronic device 102 or the server 104. In response, the device of the database 106 may be configured to retrieve and provide the queried biological signal to the electronic device 102 or the server 104, based on the received query.

In some embodiments, the database 106 may be hosted on a plurality of servers stored at the same or different locations. The operations of the database 106 may be executed using hardware including a processor, a microprocessor (e.g., to perform or control performance of one or more operations), a field-programmable gate array (FPGA), or an application-specific integrated circuit (ASIC). In some other instances, the database 106 may be implemented using software.

The communication network 108 may include a communication medium through which the electronic device 102 and the server 104 may communicate with one another. The communication network 108 may be one of a wired connection or a wireless connection. Examples of the communication network 108 may include, but are not limited to, the Internet, a cloud network, Cellular or Wireless Mobile Network (such as Long-Term Evolution and $5^{th}$ Generation (5G) New Radio (NR)), satellite communication system (using, for example, low earth orbit satellites), a Wireless Fidelity (Wi-Fi) network, a Personal Area Network (PAN), a Local Area Network (LAN), or a Metropolitan Area Network (MAN). Various devices in the network environment 100 may be configured to connect to the communication network 108 in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

The pre-trained neural network model 110 may be a computational network or a system of artificial neurons, arranged in a plurality of layers, as nodes that may be configured to detect the first peak and the first trough of the received biological signal. The plurality of layers of the neural network may include an input layer, one or more hidden layers, and an output layer. Each layer of the plurality of layers may include one or more nodes (or artificial neurons, represented by circles, for example). Outputs of all nodes in the input layer may be coupled to at least one node of hidden layer(s). Similarly, inputs of each hidden layer may be coupled to outputs of at least one node in other layers of the neural network. Outputs of each hidden layer may be coupled to inputs of at least one node in other layers of the neural network. Node(s) in the final layer may receive inputs from at least one hidden layer to output a result. The number of layers and the number of nodes in each layer may be determined from hyper-parameters of the neural network. Such hyper-parameters may be set before, while training, or after training the neural network on a training dataset.

Each node of the pre-trained neural network model 110 may correspond to a mathematical function (e.g., a sigmoid function or a rectified linear unit) with a set of parameters, tunable during training of the network. The set of parameters may include, for example, a weight parameter, a regularization parameter, and the like. Each node may use the mathematical function to compute an output based on one or more inputs from nodes in other layer(s) (e.g., previous layer(s)) of the neural network. All or some of the nodes of the neural network may correspond to same or a different mathematical function.

In training of the pre-trained neural network model 110, one or more parameters of each node of the neural network may be updated based on whether an output of the final layer for a given input (from the training dataset) matches a correct result based on a loss function for the neural network. The above process may be repeated for same or a different input until a minima of loss function may be achieved and a training error may be minimized. Several methods for training are known in art, for example, gradient descent, stochastic gradient descent, batch gradient descent, gradient boost, meta-heuristics, and the like.

The pre-trained neural network model 110 may include electronic data, which may be implemented as, for example, a software component of an application executable on the electronic device 102. The pre-trained neural network model 110 may rely on libraries, external scripts, or other logic/instructions for execution by a processing device. The pre-trained neural network model 110 may include code and routines configured to enable a computing device to perform one or more operations. Additionally or alternatively, the pre-trained neural network model 110 may be implemented using hardware including a processor, a microprocessor (e.g., to perform or control performance of one or more operations), a field-programmable gate array (FPGA), or an application-specific integrated circuit (ASIC). Alternatively, in some embodiments, the neural network may be implemented using a combination of hardware and software.

In an embodiment, the pre-trained neural network model 110 may be a scalable deep-learning model comprising an encoder model, a decoder model, and a set of convolution neural network layers. The scalable deep-learning model may take un-processed data such as, an unprocessed biological signal, to detect the first peak and the first trough. The encoder model of the present disclosure may receive the biological signal as an input. Based on the received input, the encoder model may determine a compressed feature vector associated with the biological signal. An encoded version (i.e., the compressed feature vector) of the received input biological signal may be transmitted to the decoder model. The decoder model may reconstruct the input dataset such as, the biological signal, back from the encoded version. Thus, the decoder model may decompress the compressed feature vector associated with the biological signal. Each of the set of convolution neural network layers may perform a dot product between two matrices. Herein, a first matrix also known as a kernel, may include a set of learnable parameters and a second matrix may be a portion of a receptive field associated with the corresponding convolution neural network layer. In an embodiment, a kernel size associated with each of the set of convolution neural network layers may be even. That is, the kernel size may be "2", "4", "6", "8", and so on.

In an embodiment, the scalable deep-learning model may be a machine learning (ML) model. The ML model may be trained to identify a relationship between inputs, such as, features in a training dataset, and output labels, such as, the detected first peak and the detected first trough. The ML model may be defined by its hyper-parameters, for example, number of weights, cost function, input size, number of layers, and the like. The parameters of the ML model may be tuned and weights may be updated so as to move towards a global minima of a cost function for the ML model. After several epochs of the training on the feature information in the training dataset, the ML model may be trained to output the first peak and the first trough from for the biological signal.

The ML model may include electronic data, which may be implemented as, for example, a software component of an application executable on the electronic device 102. The ML model may rely on libraries, external scripts, or other logic/instructions for execution by a processing device. The ML model may include code and routines configured to enable a computing device, such as the electronic device 102 to perform one or more operations such as, the detection of the first peak and the first trough, Additionally or alternatively, the ML model may be implemented using hardware including a processor, a microprocessor (e.g., to perform or control performance of one or more operations), a field-programmable gate array (FPGA), or an application-specific integrated circuit (ASIC). Alternatively, in some embodiments, the ML model may be implemented using a combination of hardware and software.

The sensor 112 may include suitable logic, circuitry, and interfaces that may be configured to capture a biological signal of the user 116. In an embodiment, the sensor 112 may be an electroencephalogram (EEG) sensor. The EEG sensor may measure a spontaneous electrical activity of a brain of the user 116. For example, the EEG senor may include a set of electrodes that may be positioned on a scalp of the user 116 to measure the EEG. In another embodiment, the sensor 112 may be an electrocardiogram (ECG) sensor. The ECG sensor may measure an electrical activity of a heart of the user 116. For example, the ECG senor may include a set of electrodes that may be positioned on limbs and chest of the user 116 to measure the ECG.

The set of biological signals 114 may include biological signals such as, the ECG, the EEG, the EMG, and the like, associated with one or more users such as, the user 116. The set of biological signals 114 may be used to determine the health condition of the user 116. A biological signal of the set of biological signals 114 may be received by the electronic device 102 to determine the health condition of the user 116 associated with the biological signal.

In operation, the electronic device 102 may be receive the biological signal associated with the user 116. The biological signal may be an electroencephalogram (EEG), electrocardiogram (ECG), electromyogram (EMG), electrooculogram (EOG), and the like. Herein, the EEG may provide information associated with the spontaneous electrical activity of the brain of the user 116. The ECG may provide information associated with the electrical activity of the heart of the user 116. Thus, the ECG and EEG may be a graph of voltage of an electrical activity of the brain/heart, respectively, versus time. In an example, the electronic device 102 may retrieve the biological signal from the database 106. In another example, the electronic device 102 may receive the biological signal measured from the sensor 112. Details related to the biological signal are further described, for example, in FIG. 3.

The electronic device 102 may detect the first peak and the first trough associated with the first peak, from the received biological signal. It may be appreciated that a peak of a signal may be a maximum amplitude of the signal and the trough of the signal may be a minimum amplitude of the signal. In an example, the received biological signal may be the ECG and the first peak may be a maximum voltage in the ECG. Details related to the detection of the first peak and the first trough are further described, for example, in FIG. 3.

The electronic device 102 may be configured to apply the local search algorithm on the received biological signal. It may be noted that a region around the detected first peak and a region around the detected first trough may include one or peaks and one or more troughs, respectively. The local search algorithm may search for peaks locally. That is, the local search algorithm may search peaks in the region around the detected first peak and in the region around the detected first trough. Details related to the local search algorithm are further described, for example, in FIG. 3

The electronic device 102 may be configured to refine the detected first peak and the first trough based on the application of the local search algorithm on the received biological signal. The detected first peak may be refined based on a search of a refined first peak in the region around the detected first peak. The detected first trough may be refined based on a search of a refined first trough in the region around the detected first trough. Details related to the refinement of the detected first peak and the first trough are further described, for example, in FIG. 3

The electronic device 102 may be configured to determine the health condition associated with the user 116 based on the refined first peak and the first trough. Herein, the health condition may provide information of an organ associated with the received biological signal. For example, in case the biological signal is ECG, then the refined first peak and the first trough may be analyzed to determine a heart condition of the user 116. Herein, the heart condition may be a normal condition, a moderate condition, or a severe condition. In case the heart condition is the normal condition, then the user 116 may not be suffering from cardiovascular diseases (CVDs). In case the condition is the moderate condition, then the user 116 may be moderately suffering from the CVDs such as, a heart blockage. In case the condition is the severe condition, then the user 116 may be severely suffering from the CVDs. Based on the determined health condition, appropriate medical care may be administered to the user 116. Details related to the health condition are further described, for example, in FIG. 3.

The electronic device 102 of the present disclosure may thus determine the health condition of the user 116 efficiently. The electronic device 102 may refine the detected first peak and the first trough. Thus, the refined first peak and the first trough may be optimal. Based on the refined first peak and the first trough, the electronic device 102 may determine the health condition associated with the user 116. Since the refined first peak and the first trough may be optimal, the determined health condition may be accurate. The electronic device 102 may thereby enable a robust and efficient determination of the health condition of the user 116. The electronic device 102 may be incorporated in applications such as, intelligent medical and wearable devices, to monitoring health and provide early diagnosis of cardiovascular diseases (CVDs).

Figure 2:
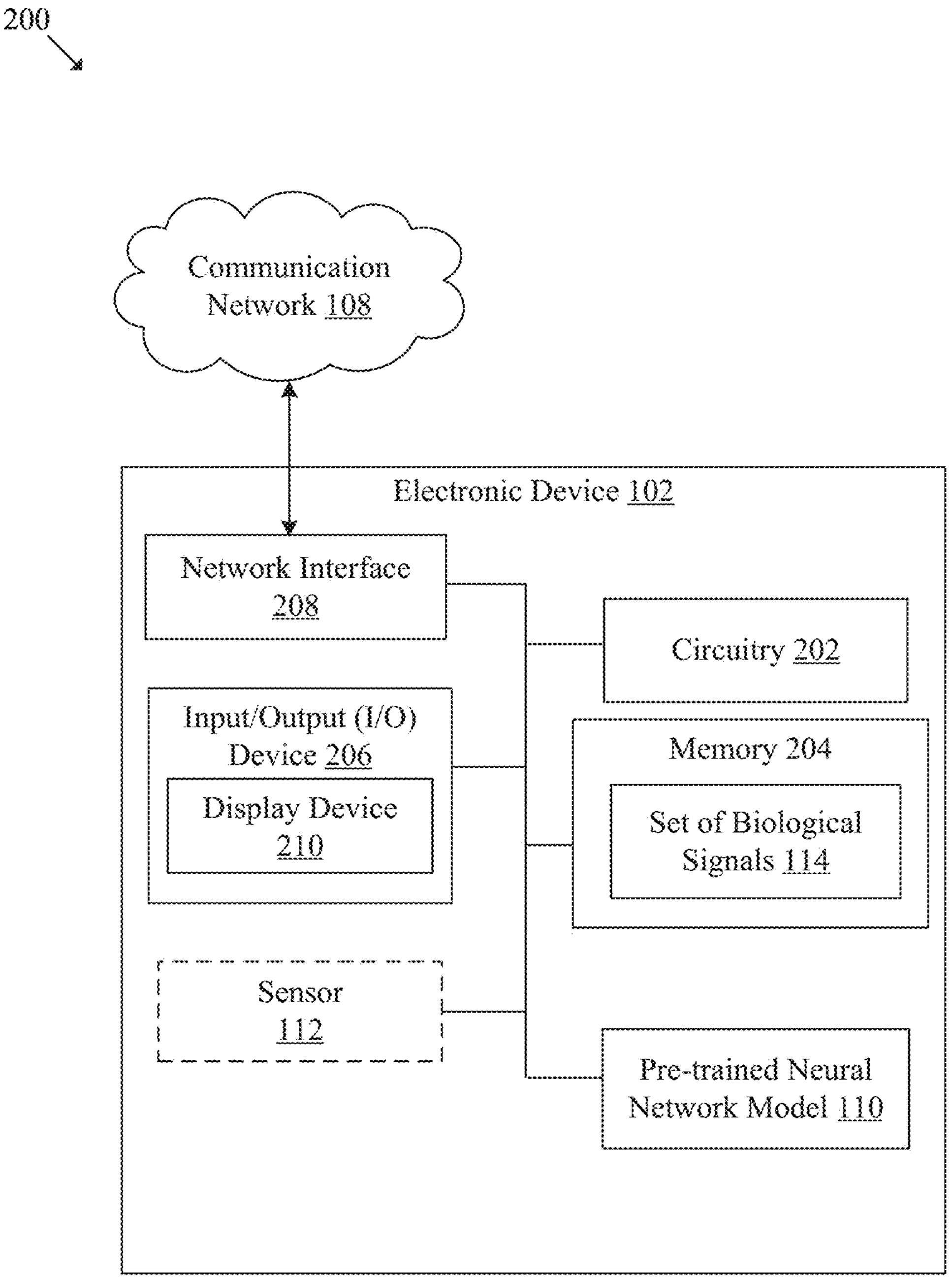
FIG. 2 is a block diagram that illustrates an exemplary electronic device of FIG. 1, in accordance with an embodiment of the disclosure.

FIG. 2 is a block diagram that illustrates an exemplary electronic device of FIG. 1, in accordance with an embodiment of the disclosure. FIG. 2 is explained in conjunction with elements from FIG. 1. With reference to FIG. 2, there is shown the exemplary electronic device 102. The electronic device 102 may include the pre-trained neural network model 110, the sensor 112, circuitry 202, a memory 204, an input/output (I/O) device 206, and a network interface 208. The memory 204 may store the set of biological signals 114. The input/output (I/O) device 206 may include a display device 210.

The circuitry 202 may include suitable logic, circuitry, and/or interfaces that may be configured to execute program instructions associated with different operations to be executed by the electronic device 102. The operations may include a biological signal reception, a low-pass filter application, a noise component removal, a first peak and a first trough detection, a local search algorithm application, a first peak and first trough refinement, and a health condition detection. The circuitry 202 may include one or more processing units, which may be implemented as a separate processor. In an embodiment, the one or more processing units may be implemented as an integrated processor or a cluster of processors that perform the functions of the one or more specialized processing units, collectively. The circuitry 202 may be implemented based on a number of processor technologies known in the art. Examples of implementations of the circuitry 202 may be an X86-based processor, a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, a central processing unit (CPU), and/or other control circuits.

The memory 204 may include suitable logic, circuitry, interfaces, and/or code that may be configured to store one or more instructions to be executed by the circuitry 202. The one or more instructions stored in the memory 204 may be configured to execute the different operations of the circuitry 202 (and/or the electronic device 102). The memory 204 may be further configured to store the set of biological signals 114. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, interfaces, and/or code that may be configured to receive an input and provide an output based on the received input. For example, the I/O device 206 may receive a first user input indicative of a selection of the biological signal from the set of biological signals 114. The I/O device 206 may be further configured to display or render the health condition associated with the selected biological signal. The I/O device 206 may include the display device 210. Examples of the I/O device 206 may include, but are not limited to, a display (e.g., a touch screen), a keyboard, a mouse, a joystick, a microphone, or a speaker. Examples of the I/O device 206 may further include braille I/O devices, such as, braille keyboards and braille readers.

The network interface 208 may include suitable logic, circuitry, interfaces, and/or code that may be configured to facilitate communication between the electronic device 102 and the server 104, via the communication network 108. The network interface 208 may be implemented by use of various known technologies to support wired or wireless communication of the electronic device 102 with the communication network 108. The network interface 208 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, or a local buffer circuitry.

The network interface 208 may be configured to communicate via wireless communication with networks, such as the Internet, an Intranet, a wireless network, a cellular telephone network, a wireless local area network (LAN), or a metropolitan area network (MAN). The wireless communication may be configured to use one or more of a plurality of communication standards, protocols and technologies, such as Global System for Mobile Communications (GSM), Enhanced Data GSM Environment (EDGE), wideband code division multiple access (W-CDMA), Long Term Evolution (LTE), $5^{th}$ Generation (5G) New Radio (NR), code division multiple access (CDMA), time division multiple access (TDMA), Bluetooth, Wireless Fidelity (Wi-Fi) (such as IEEE 802.11a, IEEE 802.11b, IEEE 802.11g or IEEE 802.11n), voice over Internet Protocol (VOIP), light fidelity (Li-Fi), Worldwide Interoperability for Microwave Access (Wi-MAX), a protocol for email, instant messaging, and a Short Message Service (SMS).

The display device 210 may include suitable logic, circuitry, and interfaces that may be configured to display or render the health condition associated with the user. The display device 210 may be a touch screen which may enable a user (e.g., the user 116) to provide a user-input via the display device 210. The touch screen may be at least one of a resistive touch screen, a capacitive touch screen, or a thermal touch screen. The display device 210 may be realized through several known technologies such as, but not limited to, at least one of a Liquid Crystal Display (LCD) display, a Light Emitting Diode (LED) display, a plasma display, or an Organic LED (OLED) display technology, or other display devices. In accordance with an embodiment, the display device 210 may refer to a display screen of a head mounted device (HMD), a smart-glass device, a see-through display, a projection-based display, an electro-chromic display, or a transparent display. Various operations of the circuitry 202 for implementation of deep-learning based peak detection in biological signal are described further, for example, in FIG. 3.

Figure 3:
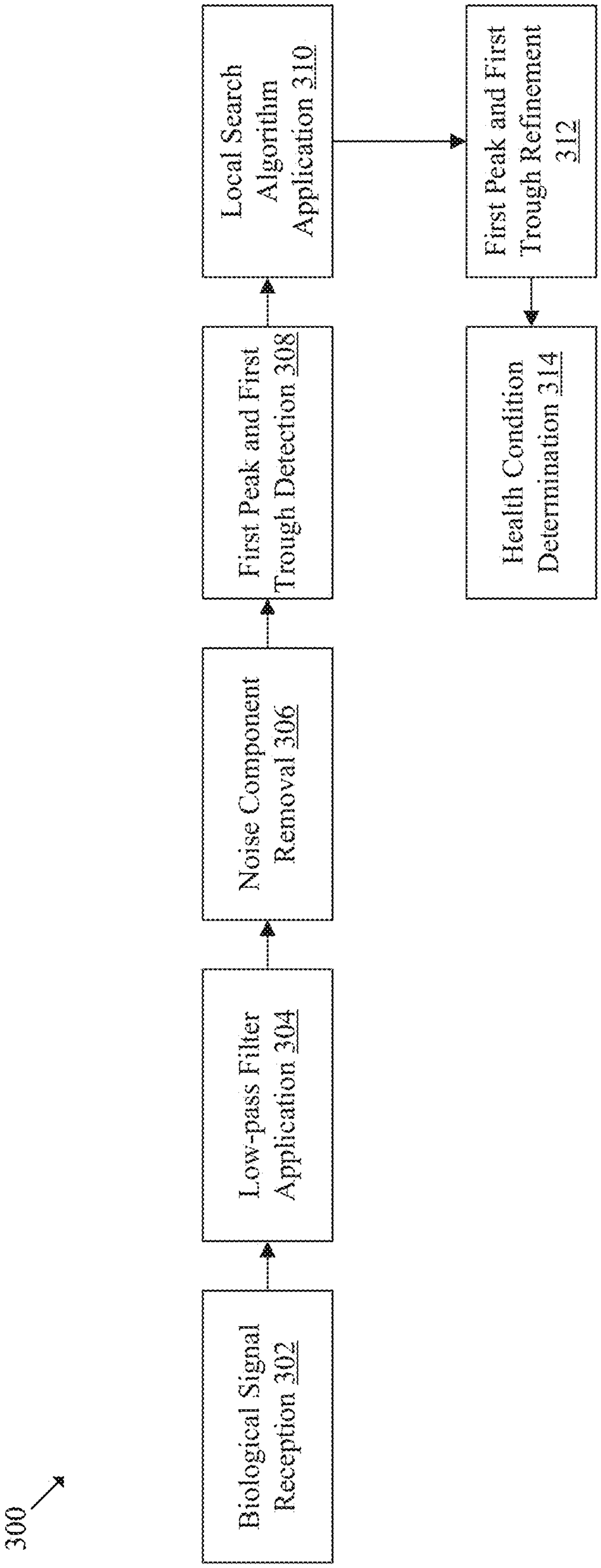
FIG. 3 is a diagram that illustrates an exemplary processing pipeline for deep-learning based peak detection in biological signal, in accordance with an embodiment of the disclosure.

FIG. 3 is a diagram that illustrates an exemplary processing pipeline for deep-learning based peak detection in biological signal, in accordance with an embodiment of the disclosure. FIG. 3 is explained in conjunction with elements from FIG. 1 and FIG. 2. With reference to FIG. 3, there is shown an exemplary processing pipeline 300 that illustrates exemplary operations from 302 to 314 for implementation of deep-learning based peak detection in biological signal. The exemplary operations 302 to 314 may be executed by any computing system, for example, by the electronic device 102 of FIG. 1 or by the circuitry 202 of FIG. 2.

At 302, an operation for biological signal reception may be executed. The circuitry 202 may be configured to receive a biological signal associated with the user 116. The biological signal may be obtained based on an electrical, chemical, and mechanical activity that may occur during a biological event. Examples, of biological event, may include, but is not limited to, an event of muscle contraction, an event of beating of heart, and the like. Examples, of biological signal include, but is not limited to, the EEG, the ECG, the EMG, an electrooculogram (EOG), an electroretinogram (ERG), and electrogastrogram (EGG).

In an embodiment, the biological signal may correspond to the ECG of the user 116. It may be appreciated that the ECG of the user 116 may be associated with the electrical activity that may occur each time the heart of user 116 beats. In order to obtain the ECG of the user 116, a plurality of sensors such as, the sensor 112 may be placed on skin of the user 116. Herein, the sensor 112 may be an electrode. In an example, ten electrodes may be placed on ten fingers and two electrodes may be placed on the chest of the user 116. Thereafter, an overall voltage measured from the twelve electrodes may be plotted against time in order to obtain the ECG of the user 116.

In an embodiment, the biological signal may correspond to an electroencephalogram (EEG) associated with the user 116. It may be appreciated that the EEG of the user 116 may be associated with the electrical activity that may occur in a brain of the user 116. It may be appreciated that brain cells of the brain of the user 116 may communicate via electrical signals. In order to obtain the EEG of the user 116, a plurality of sensors such as, the sensor 112 may be placed on a scalp of the user 116. Herein, the sensor 112 may be an electrode. Each electrode may measure voltage of the electrical signal produced by the brain cells for communicating. Thereafter, an overall voltage measured from each of the plurality of sensors may be plotted against time in order to obtain the EEG of the user 116.

At 304, an operation for low-pass filter application may be executed. The circuitry 202 may be configured to apply a low-pass filter on the received biological signal. It should be noted that the received biological signal may be noisy. The low-pass filter may be used to filter out a high frequency noise component that may be prevalent in the received biological signal. In an example, the received biological signal may be an ECG signal. Frequency range for the ECG signals of humans may be from "0.05" Hertz to "100" Hertz. High frequency noise components from "5" Hertz to "450" Hertz may be present in the received signal. In an example, a noise component that may be present in the ECG may be due to muscle tremors. Therefore, the low-pass filter may be applied on the received biological signal to filter out the noise component.

In an embodiment, the low-pass filter may correspond to a moving average filter with a predetermined window size. It may be appreciated that the moving average filter may be a finite impulse response (FIR) filter that may be used to smoothen noisy fluctuations of the received biological signal. In order to do so, the moving average filter may determine a mean over samples of the predetermined window size of the biological signal. For example, the predetermined window size may be "4". The received biological signal may be sampled into a set of samples. Thereafter, in order to determine a filtered amplitude for a first sample "A1", the moving average may determine a mean of amplitudes of a first subset of the set of samples. The first subset of the set of samples may include the first sample "A1", a second sample "A2", a third sample "A3", and a fourth sample "A4". Next, the determined moving average may be taken as the amplitude of the first sample "A1. Similarly, the filtered amplitude for the second sample "A2" may be determined by taking a mean of amplitudes of a second subset of the set of samples. The second subset of the set of samples may include the second sample "A2", the third sample "A3", the fourth sample "A4", and a fifth sample "A5". The process may be repeated until each subset of the set of samples of the received biological signal is covered. Herein, each subset may be of size "4". That is, each subset may include "4" samples from the set of samples.

At 306, an operation for noise component removal may be executed. The circuitry 202 may be configured to remove the noise component from the received biological signal to determine a denoised signal, based on the application of the low-pass filter on the received biological signal. As discussed, the low-pass filter may filter the noise component from the received biological signal such that the filtered biological signal may be the denoised signal.

At 308, an operation for a first peak and a first trough detection may be executed. The circuitry 202 may be configured to detect the first peak and the first trough associated with the first peak, from the received biological signal. It may be appreciated that a peak of a signal may be the maximum amplitude of the signal and the trough of the signal may be the minimum amplitude of the signal. In an embodiment, the first peak and the first trough may be detected based on the denoised signal. Herein, the first peak and the first trough may be accurate due to an absence of the noise component of the original biological signal from the denoised signal. In case the noise component is not removed and the first peak and the first trough is detected from the received biological signal, then the detected first peak and the first trough may be as accurate.

In an embodiment, the biological signal may correspond to the ECG of the user 116. Herein, the first peak may correspond to a peak of at least one of a P-wave associated with the ECG, an R-wave associated with the ECG, a T-wave associated with the ECG, and the first trough may correspond to a trough of at least one of a Q-wave associated with the ECG, or an S-wave associated with the ECG. The P-wave may be associated with electrical impulses generated in a sinoatrial node of the heart of the user 116. The duration of the P-wave may be a time taken for atrial depolarization. A duration of a normal P-wave may be between 120 milliseconds to 200 milliseconds. A P-peak may be a peak of the P-wave. The R-wave may be associated with a depolarization of a main portion of ventricles of the heart of user 116. As walls of the ventricles of the heart of user 116 may be thick, hence more voltage may be required. Therefore, the R-wave may be a longest wave of the ECG. The R-peak may be a peak of the R-wave. The T-wave may be associated with a repolarization of the ventricles of the heart of user 116. The T-wave may be rounder and larger than the P-wave but smaller than the R-wave. A T-peak may be a peak of the T-wave. The Q-wave associated with the ECG may be a first negative deflection after the P-wave and may provide information of an initial depolarization of an interventricular septum of the heart of user 116. A Q-trough may be a trough of the Q-wave. The S-wave associated with the ECG may provide information of a final depolarization of the ventricles of the heart of user 116. A S-trough may be a trough of the S-wave.

In an embodiment, the biological signal may correspond to the EEG associated with the user 116. Herein, the first peak may correspond to an alpha-wave peak associated with the EEG. It may be appreciated that the alpha-wave peak may be a peak of the alpha-wave. The alpha-wave may be observed when the user 116 may be resting in a wakeful state. Typically, frequency range for the alpha-wave may be from "7.5" Hertz to "13" Hertz and the amplitude may be usually less than "50" micro-volts. The alpha-wave peak may be used to determine a brain condition of the user 116.

In an embodiment, the circuitry 202 may be further configured to apply the pre-trained neural network model 110 on the received biological signal, wherein the detection of the first peak and the first trough may be based on the application of the pre-trained neural network model 110 on the received biological signal. Herein, the pre-trained neural network model 110 may analyze the received biological signal. As the received biological signal may be a voltage versus time graph, a peak may be point on the voltage versus time graph having maximum value of the voltage and a trough may be point on the voltage versus time graph having minimum value of the voltage. It may be noted that the received biological signal may include a number of peaks and troughs. The pre-trained neural network model 110 may analyze the received biological signal to detect the first peak and the first trough. For example, in case the biological signal is the ECG, then the pre-trained neural network model 110 may analyze the received biological signal to detect the first peak as the R-peak and the first trough as the Q-trough. In an embodiment, the pre-trained neural network model 110 may detect only the first peak such as, the R-peak from the received biological signal. In another embodiment, the pre-trained neural network model 110 may detect only the first trough such as, the S-trough from the received biological signal.

In an embodiment, the pre-trained neural network model 110 may be a scalable deep-learning model comprising an encoder model, a decoder model, and a set of convolution neural network layers. The scalable deep-learning model may be a machine learning model that may take un-processed data such as, an unprocessed biological signal. The scalable deep-learning model may itself perform a process of extraction of features associated with the data (e.g., the input biological signals). Thus, a human intervention may be eliminated. The encoder model may include suitable logic, interfaces, and/or code that may be configured to compress an input dataset comprising training data, validation data, and test data. The compressed input dataset may be an encoded version of the input dataset. The encoder model of the present disclosure may receive the biological signal or the denoised signal as an input. Based on the received input, the encoder model may determine a compressed feature vector associated with the biological signal. The encoded version may be transmitted to the decoder model. Upon reception of the encoded version, the decoder model may reconstruct the input dataset such as, the biological signal back from the encoded version. Thus, the decoder model may decompress the compressed feature vector associated with the biological signal. Each of the set of convolution neural network layers may perform a dot product between two matrices. Herein, a first matrix also known as a kernel, may include a set of learnable parameters and a second matrix may be a portion of a receptive field associated with the corresponding convolution neural network layer. In an embodiment, a kernel size associated with each of the set of convolution neural network layers may be even. That is, the kernel size may be "2", "4", "6", "8", and so on.

In an embodiment, the circuitry 202 may be further configured to receive a dataset comprising a set of biological signal recordings associated with a set of patients suffering from a health condition, wherein the neural network model may be pre-trained based on the received dataset. For example, the set of biological signal recordings may include ECG recordings of a set of patients suffering from heart diseases. Herein, the biological signal recording for each of the set of patients suffering from heart diseases may be captured via the sensor 112 and stored in the database 106, as the set of biological signal recordings. The set of biological signal recordings may be then used to pre-train the neural network model 110 based on training methods such as, but not limited to, an unsupervised method, a supervised method, and a stochastic gradient descent method.

In an embodiment, the circuitry 202 may be further configured to transform the received biological signal into a distance transform (DT) map, wherein the detection of the first peak and the first trough may be based on the distance transform (DT) map. It may be appreciated that the DT map for an image may be determined based on an assignment of each pixel of the image with a value corresponding to a distance of the corresponding pixel from a nearest obstacle pixel. In some cases, the obstacle pixels may be pixels of a boundary of the image. The DT map for the received biological signal may transform the received biological signal such that a non-feature component of the received biological signal may be assigned a new value corresponding to a distance to a nearest feature component of the received biological signal. Thus, the DT map may be used to determine whether a sample of the received biological signal within a section of the received biological signal. For example, in case the received biological signal is the ECG and R-peak of the ECG needs to be determined, then the DT map for the received biological signal may be obtained by taking R-peaks of the ECG as the boundary. Thus, the DT map for received biological signal may provide the distance of each sample of the received biological signal from a nearest R-peak. Thereafter, location of a first R-peak may be determined based on the DT map.

At 310, an operation for a local search algorithm application may be executed. The circuitry 202 may be configured to apply the local search algorithm on the received biological signal. It may be noted that a region around the detected first peak and a region around the detected first trough may include one or peaks and one or more troughs, respectively. Thus, the detected first peak and the detected first trough may not be optimum and may need to be further refined based on an application of the local search algorithm. In an example, the local search algorithm may be a hill climbing algorithm that may iterate continuously in a direction of increasing value to determine the refined first peak. The local search algorithm may terminate when values of the neighborhood samples are lesser than the refined first peak.

In an embodiment, the local search algorithm may correspond to a local minimum and maximum search algorithm. Herein, the local minimum and maximum search algorithm may determine a minimum in the region around the detected first trough and a maximum in the region around the detected first peak. That is, the local search algorithm may search for minima and maxima locally and not globally.

At 310, an operation for refining the detected first peak and the first trough may be executed. The circuitry 202 may be configured to refine the detected first peak and the first trough based on the application of the local search algorithm on the received biological signal. As discussed, the detected first peak and the first trough may be sub-optimal and may need to be refined. Herein, the local search algorithm may be applied in the region around the detected first trough to determine a value that is minimum in the region around the detected first trough. The determined value that is a minimum in the region around the detected first trough may be the refined first trough. Similarly, the local search algorithm may be applied in the region around the detected first peak to determine a value that is maximum in the region around the detected first peak. The determined value that is a maximum in the region around the detected first peak may be the refined first peak.

In an embodiment, the detected first peak and the first trough may be refined further based on baseline information associated with the received biological signal. The baseline information may be an equation of a baseline value of the biological signal. The baseline may be a straight line parallel to a time axis of the received biological signal. The baseline may be used as a reference to refine the first peak and the first trough. The detected first peak and the first trough may be refined such that the refined first peak may be greater that the voltage of the first baseline and the refined first trough may be lesser that the voltage of the first baseline.

At 312, an operation for a health condition determination may be executed. The circuitry 202 may be configured to determine the health condition associated with the user 116 based on the refined first peak and the first trough. The health condition may provide information associated with a health of the user 116. In an example, the health condition may be a normal condition, a moderate condition, or a severe condition. The health condition may be rendered on a display device, such as, the display device 210 of FIG. 2 to notify the user 116 or a healthcare professional. Based on the notified health condition, appropriate treatment may be administered to the user 116.

In an embodiment, the health condition associated with the user 116 may be at least one of a heart condition associated with the user 116 or a brain condition associated with the user 116. In case the biological signal is the ECG of the user 116, then the heart condition associated with the user 116 may be determined. In an example, the heart condition may be a normal condition, a moderate condition, or a severe condition. The heart condition may be the normal condition in case the heart of user 116 is determined to be functioning normally. The heart condition may be the moderate condition in case the user 116 is suffering from moderate heart diseases and the heart of the user 116 is functioning abnormally. The heart condition may be the severe condition in case the user 116 is suffering from severe heart diseases and the heart of the user 116 is functioning abnormally. However, in case the biological signal is the EEG of the user 116, then the brain condition associated with the user 116 may be determined. In an example, the brain condition may be a normal condition, a moderate condition, or a severe condition. The brain condition may be the normal condition in case the brain of user 116 is determined to be functioning normally. The brain condition may be the moderate condition in case the user 116 is suffering from moderate brain diseases and the brain of the user 116 is functioning abnormally. The brain condition may be the severe condition in case the user 116 is suffering from severe brain diseases and the brain of the user 116 is functioning abnormally.

The electronic device 102 of the present disclosure may provide an automatic and robust peak detection framework for a noisy and irregular biological signal. The detected first peak and the detected first trough may be immune to noise component prevalent in the received biological signal as the received biological signal may be filtered to remove the noise component prior to detection of the first peak and the first trough. Further, the electronic device 102 may refine the detected first peak and the first trough based on the application of the local search algorithm on the received biological signal. The refined first peak and the first trough may be thus optimal. Based on the refined first peak and the first trough, the electronic device 102 may determine the health condition associated with the user 116. Since the refined first peak and the first trough may be optimal, the determined health condition may be accurate. The disclosed electronic device 102 may be thus enable a robust and efficient determination of the health condition of the user 116. Therefore, the disclosed electronic device 102 may be incorporated in applications such as, intelligent medical and wearable devices, to monitor health of users and provide early diagnosis of diseases, such as, cardiovascular diseases (CVDs).

Figure 4A:
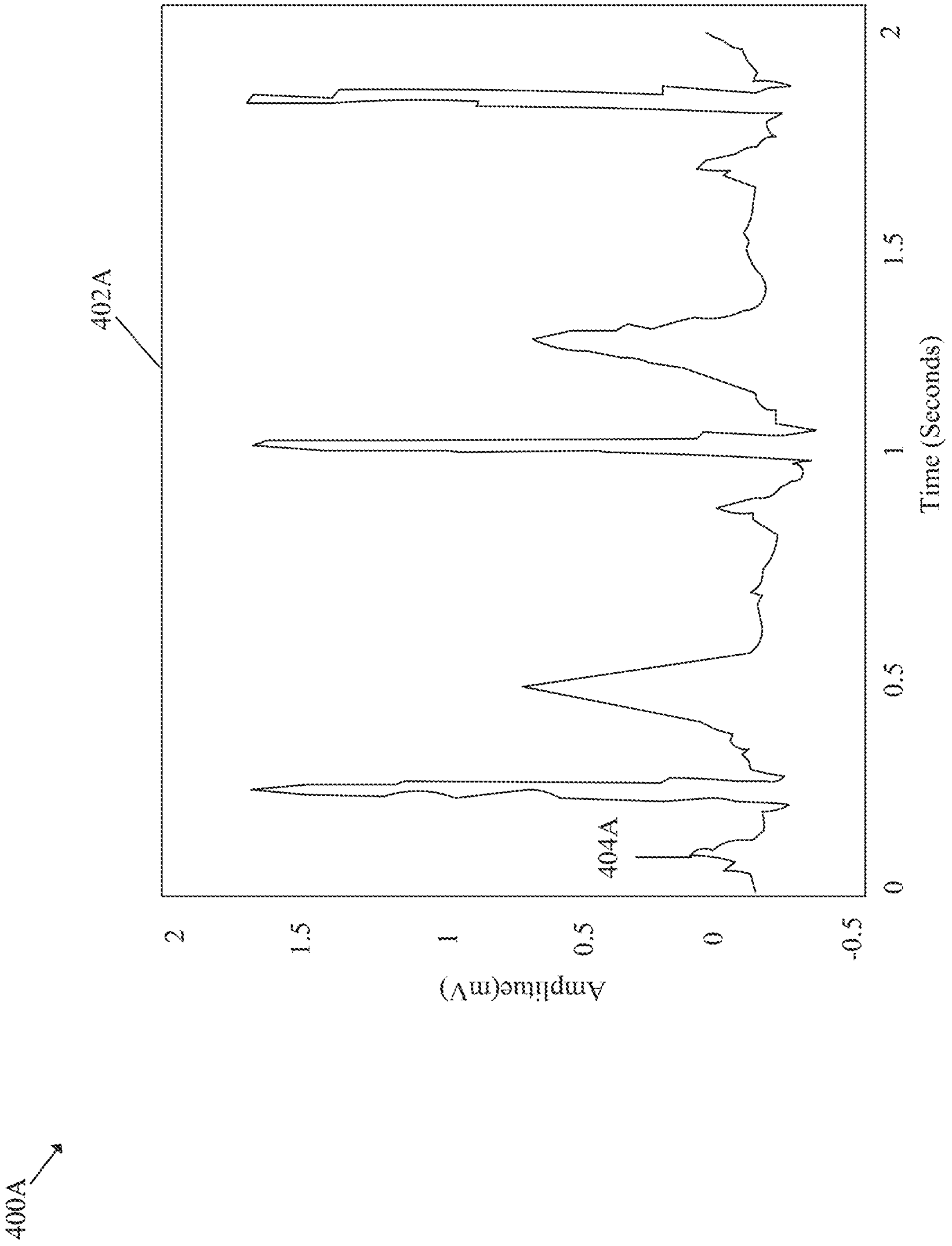
FIG. 4A is a diagram that illustrates an exemplary scenario of a normal ECG, in accordance with an embodiment of the disclosure.

FIG. 4A is a diagram that illustrates an exemplary scenario of a normal ECG, in accordance with an embodiment of the disclosure. FIG. 4A is described in conjunction with elements from FIG. 1, FIG. 2, and FIG. 3. With reference to FIG. 4A, there is shown an exemplary scenario 400A. The scenario 400A may include an ECG 402A. The scenario 400A further illustrates an exemplary peak 404A. A set of operations associated the scenario 400A is described herein.

In the scenario 400A of FIG. 4A, the ECG 402A is a graph of amplitude versus time. Since the ECG may be the electrical activity that may occur each time the heart of user 116 beats, the amplitude of the ECG 402A may be a voltage. The voltage may be represented in milli-volts (mV) along a vertical axis of the ECG 402A, and the time may be represented in seconds along a horizontal axis of the ECG 402A.

It may be noted that an ECG may be a normal ECG in case an amplitude of the P-wave of the ECG is lesser than "0.25" milli-volts and a duration of the P-wave is less than "0.12" seconds. Furthermore, a heart rate in beats per minute may be "60" to "100" beats per minute for a normal ECG. With reference to FIG. 4A, the amplitudes of the P-waves of the ECG 402A may be lesser than "0.25" milli-volts. For example, a peak 404A of the P-wave of the ECG 402A may be approximately 0.125 milli-volts. Hence, the ECG 402A may be the normal ECG. That is, the heart condition of a patient such as, the user 116 associated with the ECG 402A may be normal. In other words, the heart of the user 116 may be functioning normally.

It should be noted that scenario 400A of FIG. 4A is for exemplary purposes and should not be construed to limit the scope of the disclosure.

Figure 4B:
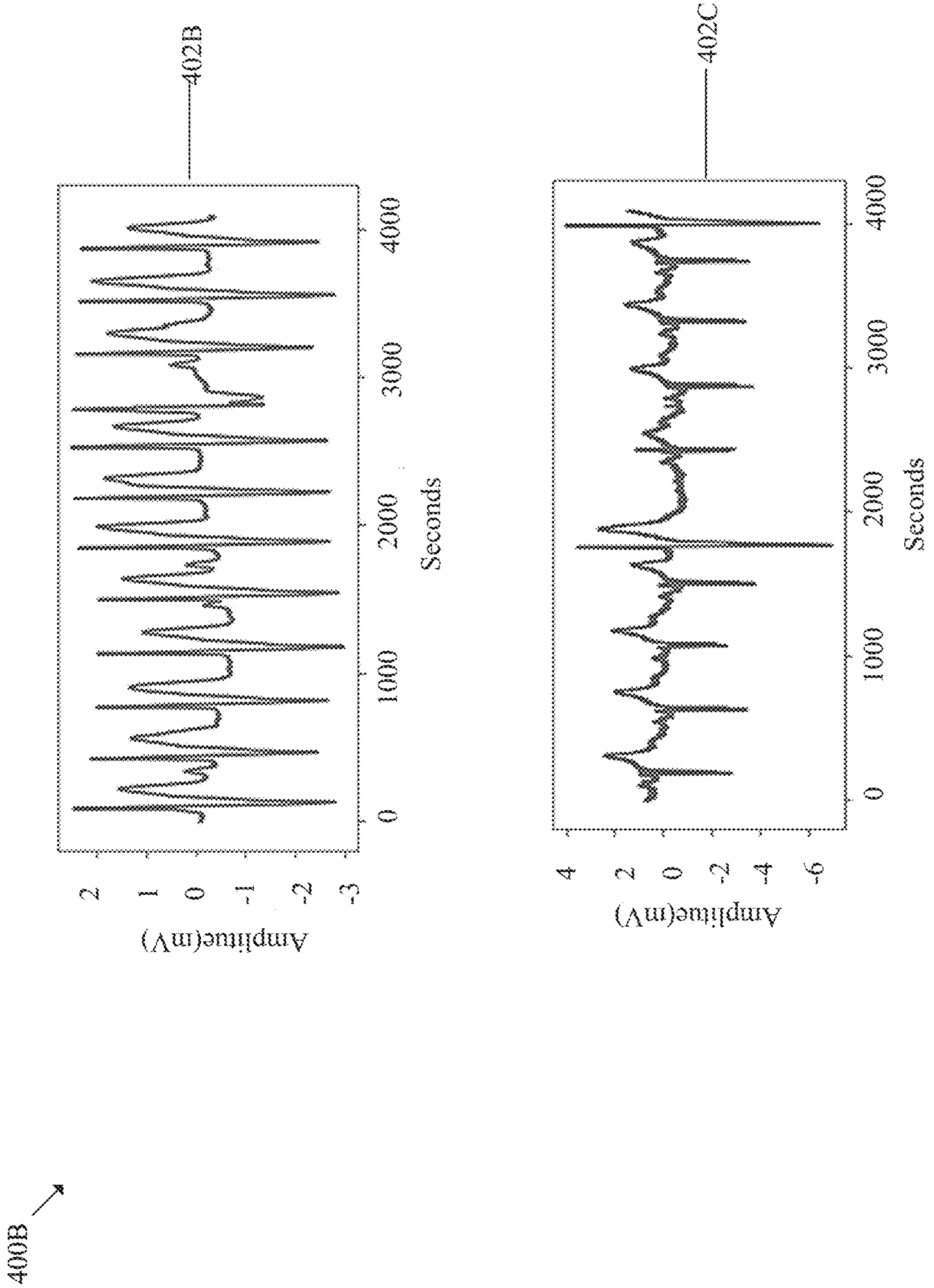
FIG. 4B is a diagram that illustrates an exemplary scenario of abnormal ECGs, in accordance with an embodiment of the disclosure.

FIG. 4B is a diagram that illustrates an exemplary scenario of abnormal ECGs, in accordance with an embodiment of the disclosure. FIG. 4B is described in conjunction with elements from FIG. 1, FIG. 2, FIG. 3, and FIG. 4A. With reference to FIG. 4B, there is shown an exemplary scenario 400B. The scenario 400B may include an ECG 402B and an ECG 402C. A set of operations associated the scenario 400B is described herein.

In the scenario 400B of FIG. 4B, the ECG 402B and the ECG 402C may be graphs of amplitude versus time. Herein, the amplitude may be the voltage that may be represented in milli-volts (mV) along the vertical axis of the ECG 402B and the ECG 402C. The time may be represented in seconds along the horizontal axis of the ECG 402B and the ECG 402C. The ECG 402B may be associated with a first user and the ECG 402C may be associated with a second user.

With reference, to FIG. 4B, the amplitude of one or more P-waves of the ECG 402B and the ECG 402C may be greater than "0.25" milli-volts. Hence, the ECG 402B and the ECG 402C may be the abnormal ECGs. That is, the heart condition of the first user and the second user associated with the ECG 402B and the ECG 402C respectively may be abnormal. In other words, the heart of the user 116 may be functioning abnormally. Therefore, the heart condition may be determined as an abnormal condition for the first user and the second user. Proper treatment may be prescribed to the first user and the second user in order to rectify abnormalities.

It should be noted that scenario 400B of FIG. 4B is for exemplary purposes and should not be construed to limit the scope of the disclosure.

Figure 5A:
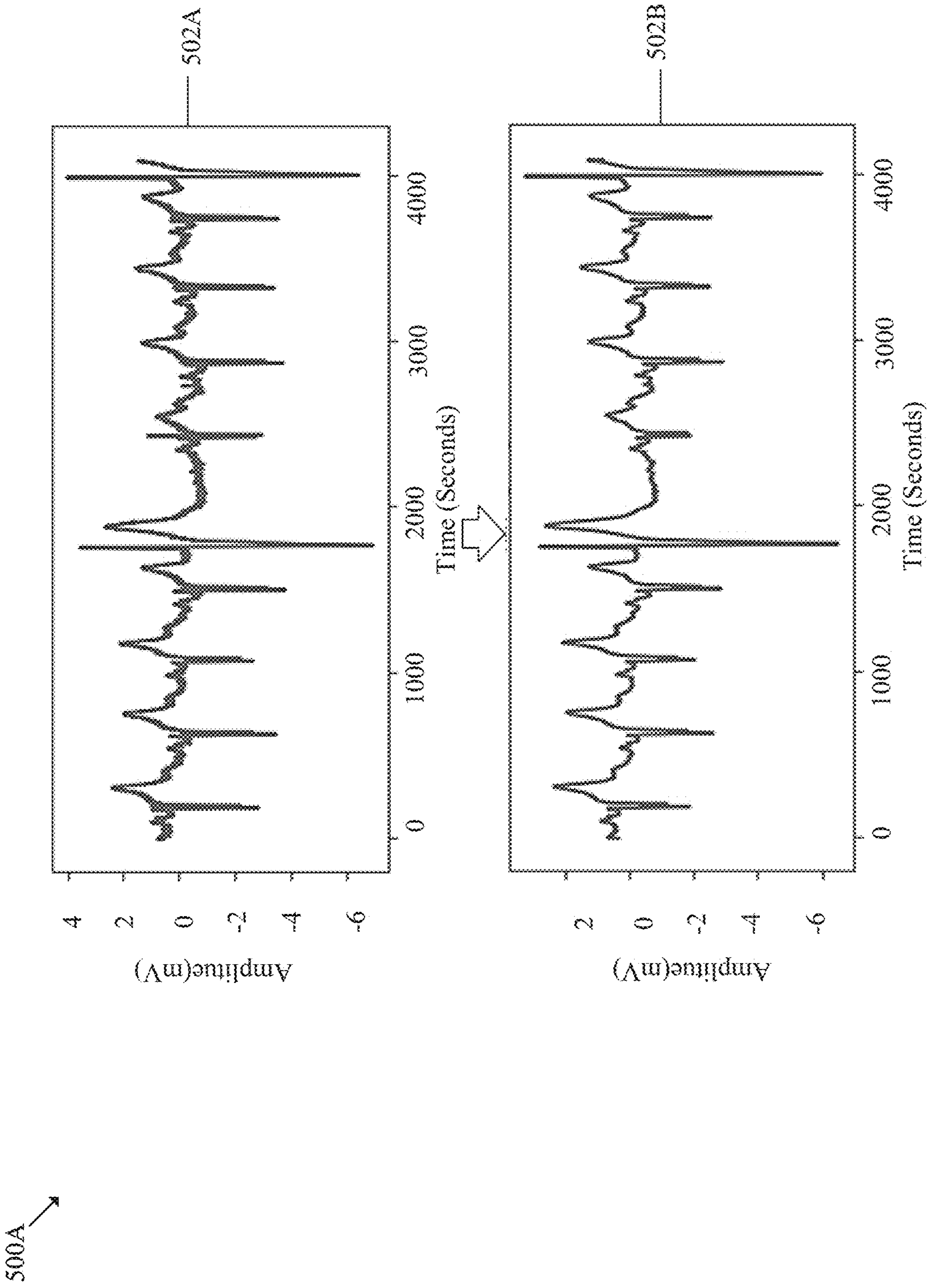
FIGS. 5A and 5B are diagrams that illustrates an exemplary scenario for removal of a noise component from ECGs, in accordance with an embodiment of the disclosure.
Figure 5B:
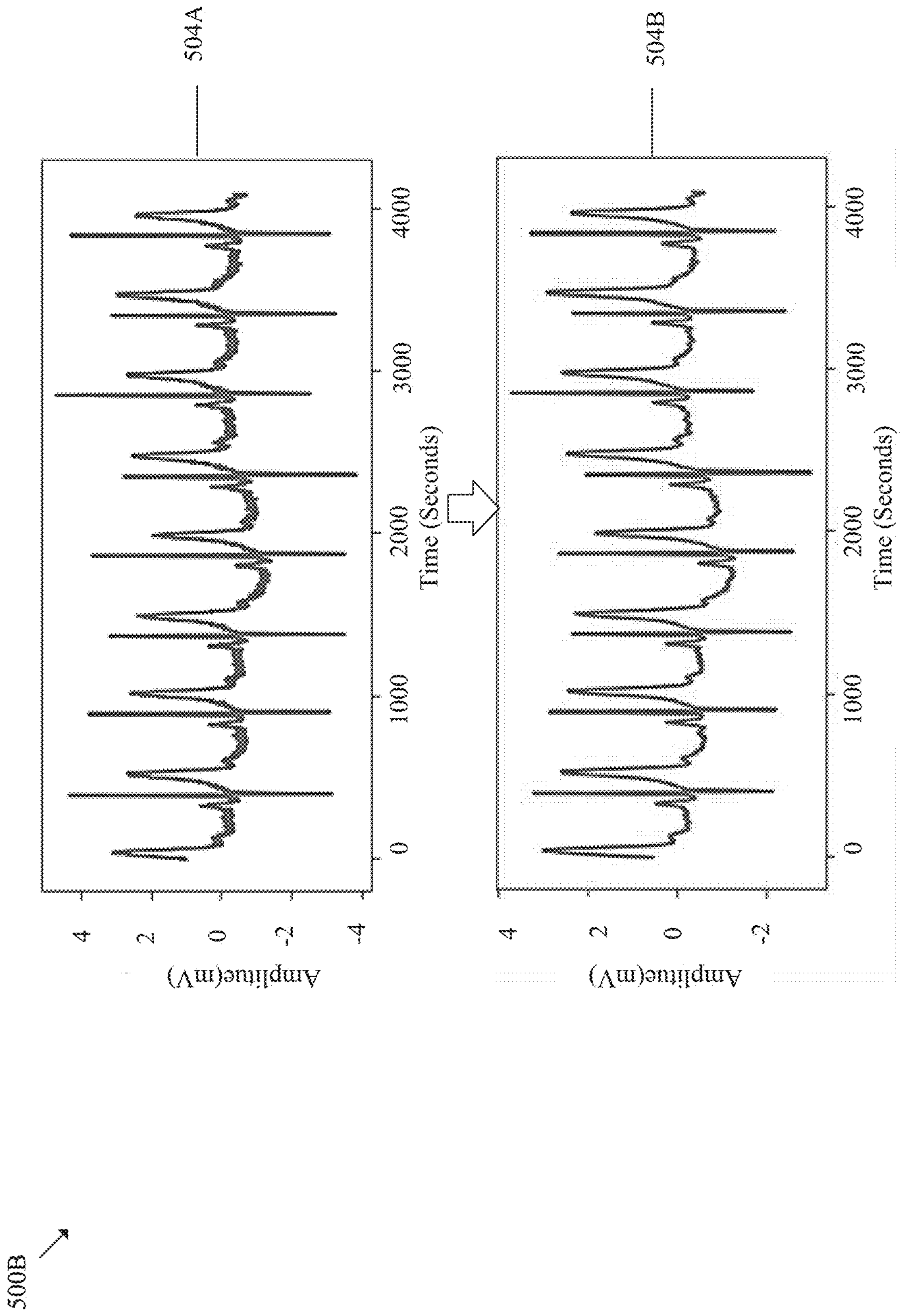

FIGS. 5A and 5B are diagrams that illustrates an exemplary scenario for removal of a noise component from ECGs, in accordance with an embodiment of the disclosure. FIGS. 5A and 5B are described in conjunction with elements from FIG. 1, FIG. 2, FIG. 3, FIG. 4A, and FIG. 4B. With reference to FIGS. 5A and 5B, there is shown exemplary scenarios 500A and 500B, respectively. The scenario 500A may include an ECG 502A and a denoised ECG 502B. Further, the scenario 500B may include an ECG 504A and a denoised ECG 504B. A set of operations associated with each of the scenarios 500A and 500B is described herein.

With reference to FIG. 5A, the ECG 502A may include noise components. Therefore, detection of a first peak and a first trough associated with the first peak, from the ECG 502A may be erroneous. In order to mitigate the aforesaid issues, a low-pass filter may be applied on the ECG 502A. Based on the application of the low-pass filter on the ECG 502A, the noise component may be removed from the ECG 502A to determine the denoised ECG 502B. For example, a moving average filter with a window size of "10" may be used to filter the ECG 502A.

With reference to FIG. 5B, the ECG 504A may include noise components. Hence, the low-pass filter may be applied on the ECG 504A. Based on the application of the low-pass filter on the ECG 504A, the noise component may be removed from the ECG 504A to determine the denoised ECG 504B.

With reference to FIGS. 5A and 5B, the denoised ECG 502B and the denoised ECG 504B may be sharper than the ECG 502A and the ECG 504A respectively. Hence, the first peaks and the first troughs that may be detected from the denoised ECG 502B and the denoised ECG 504B may be accurate. Since the detected first peaks and the first troughs may be accurate, the heart conditions of the patients associated with the ECG 502A and the ECG 504A may be determined with a higher accuracy. Details related to the low-pass filter are further described, for example, in FIG. 3.

It should be noted that scenarios 500A and 500B of FIGS. 5A and 5B, respectively, are for exemplary purposes and should not be construed to limit the scope of the disclosure.

Figure 6:
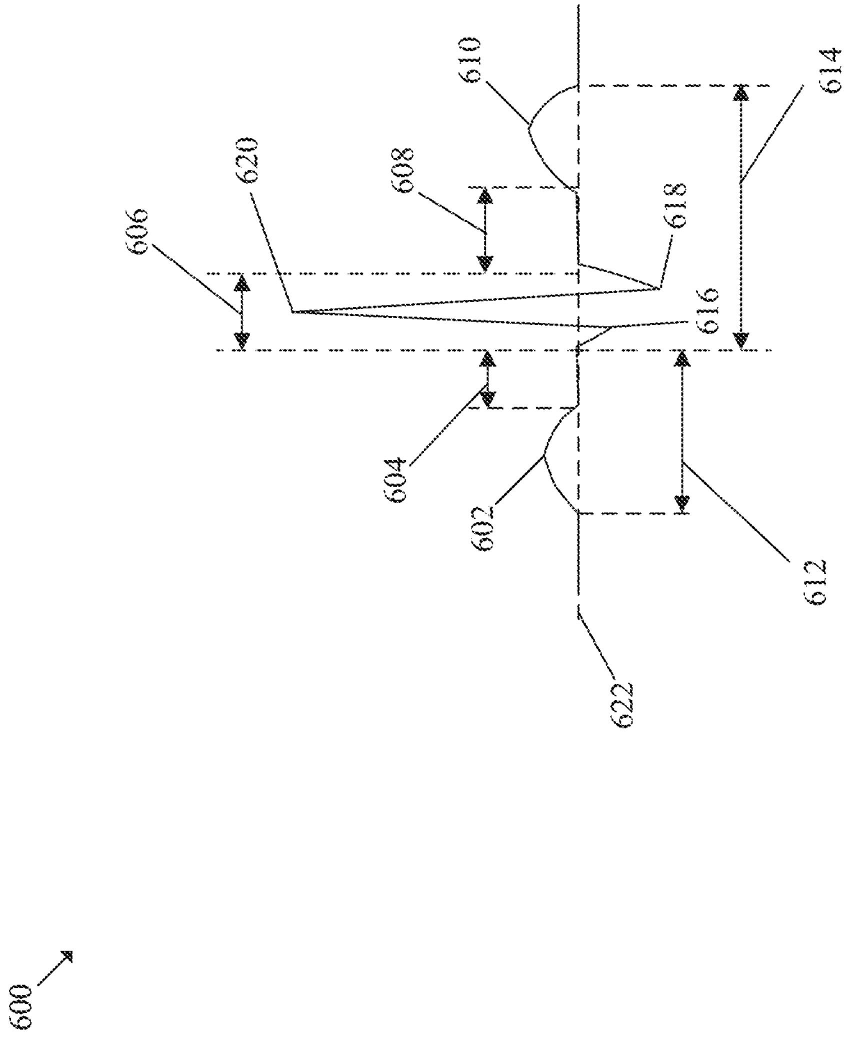
FIG. 6 is a diagram that illustrates an exemplary scenario for determination of a plurality of waves associated with an ECG, in accordance with an embodiment of the disclosure.

FIG. 6 is a diagram that illustrates an exemplary scenario for determination of a plurality of waves associated with an ECG, in accordance with an embodiment of the disclosure. FIG. 6 is described in conjunction with elements from FIG.

1, FIG. 2, FIG. 3, FIG. 4A, FIG. 4B, FIG. 5A, and FIG. 5B. With reference to FIG. 6, there is shown an exemplary scenario 600. The scenario 600 may show an ECG including a P-peak 602, a "PR" segment 604, a "QRS" complex 606, an "ST" segment 608, a T-peak 610, a "PR" interval 612, a "QT" interval 614, a Q-peak 616, an S-peak 618, an R-peak 620, and a baseline 622.

With reference to FIG. 6, the P-peak 602 may be a peak of a P-wave, the T-peak 610 may be a peak of a T-wave, the Q-peak 616 may be a peak of a Q-wave, the S-peak 618 may be a peak of a S-wave, and the R-peak 620 may be a peak of a R-wave associated with the ECG of the scenario 600. The "PR" segment 604 may be associated with the P-wave and the R-wave. The "QRS" complex 606 may include the Q-wave, the R-wave, and the S-wave of the ECG. It may be note that in adults, a time duration of the "QRS" complex 606 may be from "80" milliseconds to "100" milliseconds. The "ST" segment 608 may be associated with the S-wave and the T-wave. The "PR" interval 612 may depict a time duration of the P-wave and the R-wave of the ECG. The "QT" interval 614 may depict a time duration of the Q-wave and the T-wave of the ECG. The baseline 622 may be straight line that may be used for refinement of the detected first peak and the detected first trough.

It should be noted that scenario 600 of FIG. 6 is for exemplary purposes and should not be construed to limit the scope of the disclosure.

Figure 7:
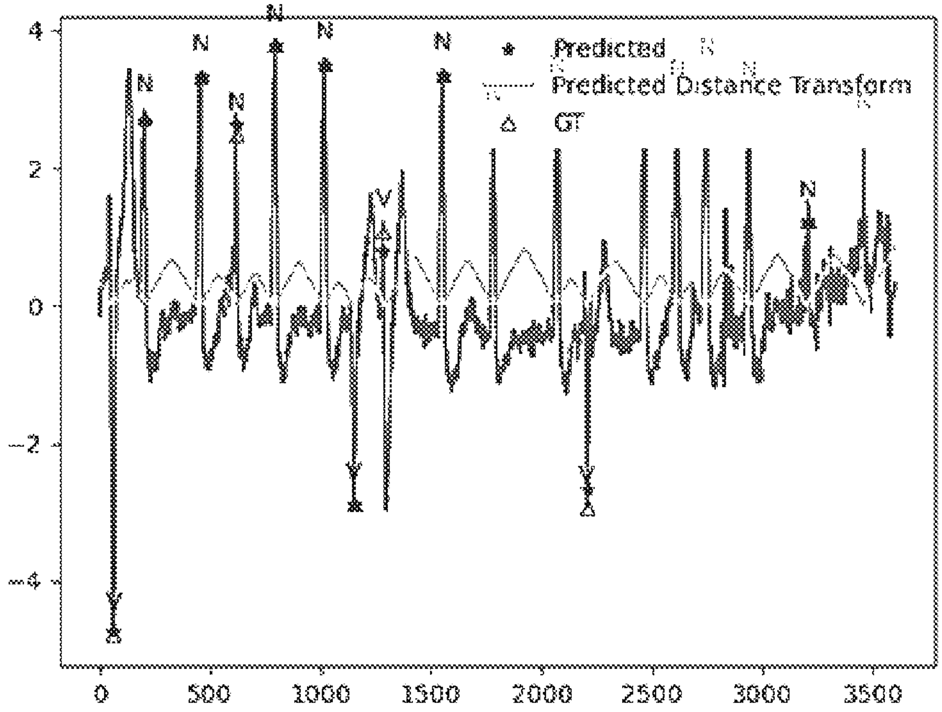
FIG. 7 is a diagram that illustrates an exemplary scenario for detection of R-peak of an ECG, in accordance with an embodiment of the disclosure.

FIG. 7 is a diagram that illustrates an exemplary scenario for detection of a R-peak of an ECG, in accordance with an embodiment of the disclosure. FIG. 7 is described in conjunction with elements from FIG. 1, FIG. 2, FIG. 3, FIG. 4A, FIG. 4B, FIG. 5A, FIG. 5B, and FIG. 6. With reference to FIG. 7, there is shown an exemplary scenario 700. The scenario 700 may include an ECG 702, a predicted DT map 704, and a set of predicted first peaks such as, a first peak 706A and a first peak 706B. A set of operations associated the scenario 700 is described herein.

In the scenario 700 of FIG. 7, the ECG 702 may be denoised to obtain the denoised signal. The denoised signal may be applied to the pre-trained neural network model 110. The pre-trained neural network model 110 may predict the set of predicted first peaks such as, a first peak 706A and a first peak 706B. Since the ECG 702 may be denoised, a process of detection of the first peak such as, the first peak 706A and the first peak 706B, may be robust to noise. Moreover, the detected first peaks such as, the first peak 706A and the first peak 706B, may be further refined based on the application of the DT map 704. The refined first peak may be then used to determine the heart condition of a patient such as, the user 116 that may be associated to the ECG 702. Details related to the DT map are further provided in for example, FIG. 3.

It should be noted that scenario 700 of FIG. 7 is for exemplary purposes and should not be construed to limit the scope of the disclosure.

Figure 8:
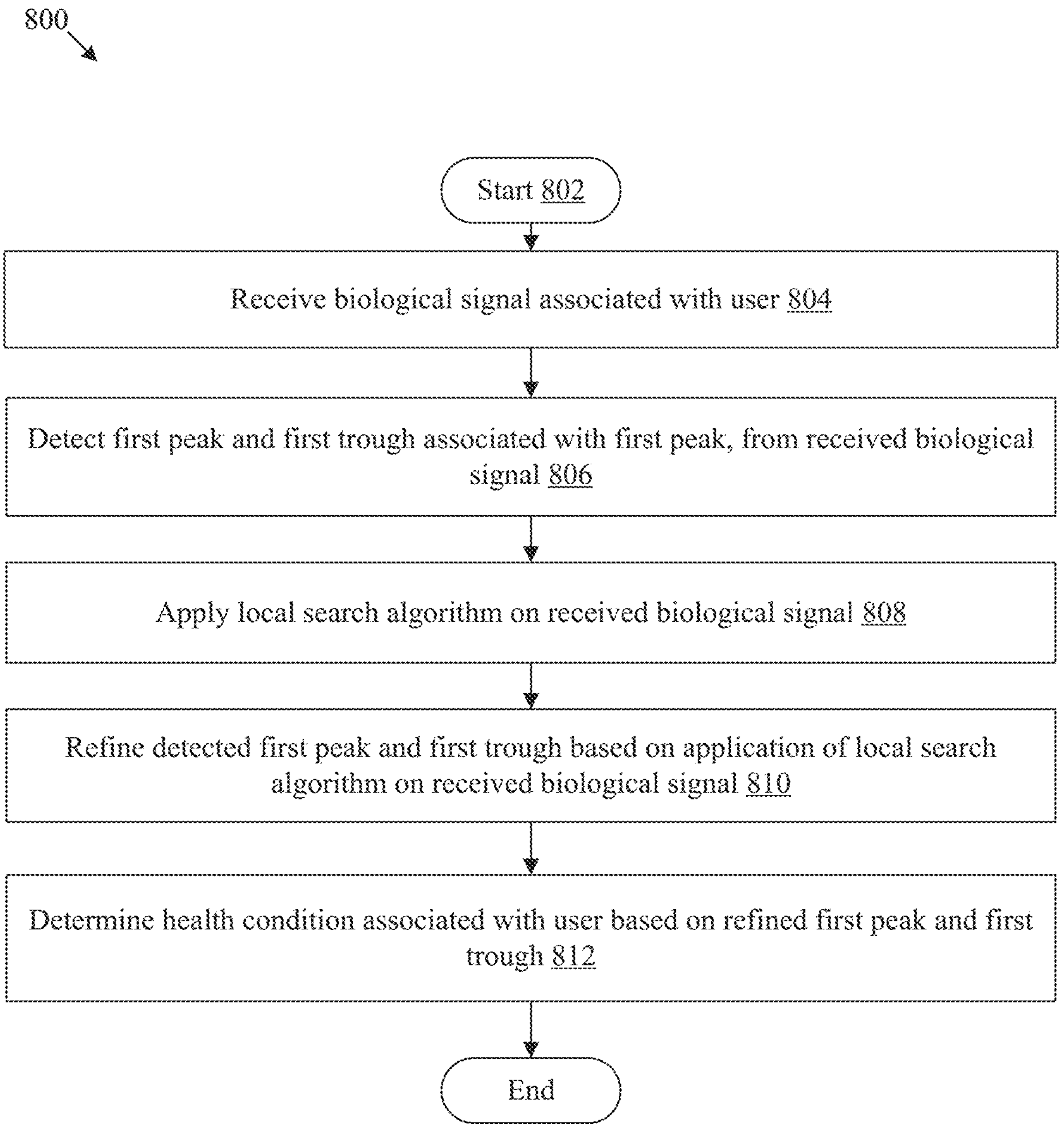
FIG. 8 is a flowchart that illustrates operations of an exemplary method for deep-learning based peak detection in biological signal, in accordance with an embodiment of the disclosure.

FIG. 8 is a flowchart that illustrates operations of an exemplary method for deep-learning based peak detection in biological signal, in accordance with an embodiment of the disclosure. FIG. 8 is described in conjunction with elements from FIG. 1, FIG. 2, FIG. 3, FIG. 4A, FIG. 4B, FIG. 5A, FIG. 5B, FIG. 6, and FIG. 7. With reference to FIG. 8, there is shown a flowchart 800. The flowchart 800 may include operations from 802 to 812 and may be implemented by the electronic device 102 of FIG. 1 or by the circuitry 202 of FIG. 2. The flowchart 800 may start at 802 and proceed to 804.

At 804, the biological signal associated with the user 116 may be received. The circuitry 202 may be configured to receive the biological signal associated with the user 116. Details related to the biological signal are further described, for example, in FIG. 3 (at 302).

At 806, the first peak and the first trough associated with the first peak may be detected from the received biological signal. The circuitry 202 may be configured to detect the first peak and the first trough associated with the first peak, from the received biological signal. Details related to the detection of the first peak and the first trough are further described, for example, in FIG. 3 (at 308, based on removal of the noise component from the received biological signal, as described, for example, at 304 and 306 in FIG. 3).

At 808, the local search algorithm may be applied on the received biological signal. The circuitry 202 may be configured to apply the local search algorithm on the received biological signal. Details related to the local search algorithm are further described, for example, in FIG. 3 (at 310).

At 810, the detected first peak and the first trough may be refined based on the application of the local search algorithm on the received biological signal. The circuitry 202 may be configured to refine the detected first peak and the first trough based on the application of the local search algorithm on the received biological signal. Details related to the refinement of the detected first peak and the first trough are further described, for example, in FIG. 3 (at 312).

At 812, the health condition associated with the user 116 may be determined based on the refined first peak and the first trough. The circuitry 202 may be configured to determine the health condition associated with the user 116 based on the refined first peak and the first trough. Details related to the health condition are further described, for example, in FIG. 3 (at 314). Control may pass to end.

Although the flowchart 800 is illustrated as discrete operations, such as, 804, 806, 808, 810, and 812 the disclosure is not so limited. Accordingly, in certain embodiments, such discrete operations may be further divided into additional operations, combined into fewer operations, or eliminated, depending on the implementation without detracting from the essence of the disclosed embodiments.

Various embodiments of the disclosure may provide a non-transitory computer-readable medium and/or storage medium having stored thereon, computer-executable instructions executable by a machine and/or a computer to operate an electronic device (for example, the electronic device 102 of FIG. 1). Such instructions may cause the electronic device 102 to perform operations that may include receipt of a biological signal associated with a user (such as, the user 116 of FIG. 1). The operations may further include detection of a first peak and a first trough associated with the first peak, from the received biological signal. The operations may further include application of a local search algorithm on the received biological signal. The operations may further include refinement of the detected first peak and the first trough based on the application of the local search algorithm on the received biological signal. The operations may further include determination of a health condition associated with the user (such as, the user 116 of FIG. 1) based on the refined first peak and the first trough.

Exemplary aspects of the disclosure may provide an electronic device (such as, the electronic device 102 of FIG. 1) that includes circuitry (such as, the circuitry 202). The circuitry 202 may be configured to receive a biological signal associated with a user (such as, the user 116 of FIG. 1). The circuitry 202 may be configured to detect a first peak and a first trough associated with the first peak, from the received biological signal. The circuitry 202 may be configured to apply a local search algorithm on the received biological signal. The circuitry 202 may be configured to refine the detected first peak and the first trough based on the application of the local search algorithm on the received biological signal. The circuitry 202 may be configured to determine a health condition associated with the user (such as, the user 116 of FIG. 1) based on the refined first peak and the first trough.

In an embodiment, the circuitry 202 may be further configured to apply a low-pass filter on the received biological signal. The circuitry 202 may be further configured to remove a noise component from the received biological signal to determine a denoised signal, based on the application of the low-pass filter on the received biological signal. The first peak and the first trough may be detected based on the determined denoised signal. In an embodiment, the low-pass filter may correspond to a moving average filter with a predetermined window size.

In an embodiment, the circuitry 202 may be further configured to apply a pre-trained neural network model (such as, the pre-trained neural network model 110 of FIG. 1) on the received biological signal, wherein the detection of the first peak and the first trough is based on the application of the pre-trained neural network model 110 on the received biological signal.

In an embodiment, the pre-trained neural network model 110 may be a scalable deep-learning model comprising an encoder model, a decoder model, and a set of convolution neural network layers. In an embodiment, a kernel size associated with each of the set of convolution neural network layers may be even.

In an embodiment, the circuitry 202 may be further configured to receive a dataset comprising a set of biological signal recordings associated with a set of patients suffering from a health condition. The neural network model may be pre-trained based on the received dataset.

In an embodiment, the circuitry 202 may be further configured to transform the received biological signal into a distance transform (DT) map. The detection of the first peak and the first trough may be based on the distance transform (DT) map.

In an embodiment, the local search algorithm may correspond to a local minimum and maximum search algorithm.

In an embodiment, the biological signal may correspond to an electrocardiogram (ECG) of the user 116.

In an embodiment, the first peak may correspond to a peak of at least one of a P-wave associated with the ECG, an R-wave associated with the ECG, a T-wave associated with the ECG, and the first trough may correspond to a trough of at least one of a Q-wave associated with the ECG, or an S-wave associated with the ECG In an embodiment, the biological signal may correspond to an electroencephalogram (EEG) associated with the user 116.

In an embodiment, the first peak may correspond to an alpha-wave peak associated with the EEG.

In an embodiment, the detected first peak and the first trough may be refined further based on baseline information associated with the received biological signal.

In an embodiment, the health condition associated with the user 116 may be at least one of a heart condition associated with the user or a brain condition associated with the user 116.

The present disclosure may also be positioned in a computer program product, which comprises all the features that enable the implementation of the methods described herein, and which when loaded in a computer system is able to carry out these methods. Computer program, in the present context, means any expression, in any language, code or notation, of a set of instructions intended to cause a system with information processing capability to perform a particular function either directly, or after either or both of the following: a) conversion to another language, code or notation; b) reproduction in a different material form.

While the present disclosure is described with reference to certain embodiments, it will be understood by those skilled in the art that various changes may be made, and equivalents may be substituted without departure from the scope of the present disclosure. In addition, many modifications may be made to adapt a particular situation or material to the teachings of the present disclosure without departure from its scope. Therefore, it is intended that the present disclosure is not limited to the embodiment disclosed, but that the present disclosure will include all embodiments that fall within the scope of the appended claims.

What is claimed is:

1. An electronic device, comprising:
circuitry configured to:
receive a biological signal associated with a user;
apply a low-pass filter on the received biological signal;
remove a noise component from the received biological signal based on the application of the low-pass filter on the received biological signal;
determine a denoised signal based on the removal of the noise component from the received biological signal;
detect each of a first peak and a first trough associated with the first peak, from the determined denoised signal;
apply a local search algorithm on the determined denoised signal;
refine each of the detected first peak and the detected first trough based on the application of the local search algorithm on the determined denoised signal; and
determine a health condition associated with the user based on the refined first peak and the refined first trough.

2. The electronic device according to claim 1, wherein the low-pass filter corresponds to a moving average filter with a specific window size.

3. The electronic device according to claim 1, wherein the circuitry is further configured to:
apply a trained neural network model on the determined denoised signal; and
detect each of the first peak and the first trough based on the application of the trained neural network model on the determined denoised signal.

4. The electronic device according to claim 3, wherein the trained neural network model is a scalable deep-learning model that comprises an encoder model, a decoder model, and a set of convolution neural network layers.

5. The electronic device according to claim 4, wherein a kernel size associated with each of the set of convolution neural network layers is even.

6. The electronic device according to claim 3, wherein
the circuitry is further configured to receive a dataset comprising a set of biological signal recordings that is associated with a set of patients,
the set of patients suffers from the health condition, and
the trained neural network model is trained based on the received dataset.

7. The electronic device according to claim 1, wherein the circuitry is further configured to:

transform the received biological signal into a distance transform (DT) map; and detect each of the first peak and the first trough based on the DT map.

8. The electronic device according to claim 1, wherein the local search algorithm corresponds to a local minimum and maximum search algorithm.

9. The electronic device according to claim 1, wherein the biological signal corresponds to an electrocardiogram (ECG) of the user.

10. The electronic device according to claim 9, wherein the first peak corresponds to a peak of at least one of a P-wave associated with the ECG, an R-wave associated with the ECG, or a T-wave associated with the ECG, and the first trough corresponds to a trough of at least one of a Q-wave associated with the ECG, or an S-wave associated with the ECG.

11. The electronic device according to claim 1, wherein the biological signal corresponds to an electroencephalogram (EEG) associated with the user.

12. The electronic device according to claim 11, wherein the first peak corresponds to an alpha-wave peak associated with the EEG.

13. The electronic device according to claim 1, wherein the circuitry is further configured to refine each of the detected first peak and the detected first trough based on baseline information associated with the received biological signal.

14. The electronic device according to claim 1, wherein the health condition associated with the user is at least one of a heart condition associated with the user or a brain condition associated with the user.

15. A method, comprising:

in an electronic device:

receiving a biological signal associated with a user;

applying a low-pass filter on the received biological signal;

removing a noise component from the received biological signal based on the application of the low-pass filter on the received biological signal;

determining a denoised signal based on the removal of the noise component from the received biological signal;

detecting, each of a first peak and a first trough that is associated with the first peak, from the determined denoised signal;

applying a local search algorithm on the determined denoised signal;

refining each of the detected first peak and the detected first trough based on the application of the local search algorithm on the determined denoised signal; and determining a health condition associated with the user based on the refined first peak and the refined first trough.

16. The method according to claim 15, further comprising:

applying a trained neural network model on the determined denoised signal; and detecting each of the first peak and the first trough based on the application of the trained neural network model on the determined denoised signal.

17. The method according to claim 15, further comprising:

transforming the determined denoised signal into a distance transform (DT) map; and detecting each of the first peak and the first trough based on the DT map.

18. A non-transitory computer-readable medium having stored thereon, computer-executable instructions that when executed by an electronic device, causes the electronic device to execute operations, the operations comprising:

receiving a biological signal associated with a user;

applying a low-pass filter on the received biological signal;

removing a noise component from the received biological signal based on the application of the low-pass filter on the received biological signal;

determining a denoised signal based on the removal of the noise component from the received biological signal;

detecting each of a first peak and a first trough that is associated with the first peak, from the determined denoised signal;

applying a local search algorithm on the determined denoised signal;

refining each of the detected first peak and the detected first trough based on the application of the local search algorithm on the determined denoised signal; and determining a health condition associated with the user based on the refined first peak and the refined first trough.

* * * * *